United States Patent
Konishi et al.

(10) Patent No.: US 8,722,377 B2
(45) Date of Patent: May 13, 2014

(54) COLOR REACTION USING TYROSINASE AND PEPTIDE

(71) Applicants: Sugiyo Co., Ltd., Ishikawa (JP); Ishikawa Prefectural Public University Corporation, Ishikawa (JP)

(72) Inventors: Yasuko Konishi, Nonoichi (JP); Ryota Ohara, Nanao (JP); Fumio Noda, Nanao (JP)

(73) Assignees: Sugiyo Co., Ltd., Ishikawa (JP); Ishikawa Prefectural Public University Corporation, Ishikawa (JP)

( * ) Notice: Subject to any disclaimer, the term of this patent is extended or adjusted under 35 U.S.C. 154(b) by 0 days.

(21) Appl. No.: 13/761,718

(22) Filed: Feb. 7, 2013

(65) Prior Publication Data
US 2013/0203149 A1    Aug. 8, 2013

(30) Foreign Application Priority Data
Feb. 8, 2012    (JP) .................................. 2012-24845

(51) Int. Cl.
*C12N 9/00*    (2006.01)

(52) U.S. Cl.
USPC ........................................ 435/189

(58) Field of Classification Search
CPC .................................................. C12N 15/8241
USPC .................................................. 435/189, 68.1
See application file for complete search history.

(56) References Cited

FOREIGN PATENT DOCUMENTS

| | | |
|---|---|---|
| JP | 2006-158304 A | 6/2006 |
| JP | 2010-115213 A | 5/2010 |

OTHER PUBLICATIONS

Wang et al., Tyrosinase maturation through the mammalian secretory pathway: bringing color to life. Pigment Cell Res. 19; 3-18, 2006.*

* cited by examiner

*Primary Examiner* — Tekchand Saidha
*Assistant Examiner* — Rama P Ramanujam
(74) *Attorney, Agent, or Firm* — Renner, Otto, Boisselle & Sklar, LLP (57) ABSTRACT

The problem to be solved by the present invention is to provide a method and a kit for easily performing a color reaction for coloration of bright green to blue colors by using tyrosinase. The above-mentioned problem was solved by providing a coloration method comprising the steps of: (a) mixing peptide and tyrosinase; (b) incubating the mixture; and (d) cryopreserving the incubated mixture; and by providing a kit for performing a color reaction, comprising: (i) peptide; and (ii) tyrosinase.

11 Claims, 2 Drawing Sheets

SEQUENCE LISTING

```
<160> NUMBER OF SEQ ID NOS: 5

<210> SEQ ID NO 1
<211> LENGTH: 1918
<212> TYPE: DNA
<213> ORGANISM: Pholiota nameko
<220> FEATURE:
<221> NAME/KEY: CDS
<222> LOCATION: (13)..(1890)
```

-continued

<400> SEQUENCE: 1

```
ccactctgag aa atg tct cgc gtt gtt atc act ggt gtt tct ggc act atc      51
              Met Ser Arg Val Val Ile Thr Gly Val Ser Gly Thr Ile
                1               5                  10 gcc aat cgt ctc gaa atc aat gat ttc gtc aag aac gac aag ttt ttc        99
Ala Asn Arg Leu Glu Ile Asn Asp Phe Val Lys Asn Asp Lys Phe Phe
 15              20                  25 tcg ctc tac att caa gct ctt cag gtt atg agc tca gtt cca cct cag       147
Ser Leu Tyr Ile Gln Ala Leu Gln Val Met Ser Ser Val Pro Pro Gln
 30              35                  40                  45 gaa aac gtc cga tcc ttc ttc cag atc ggt ggt att cac ggc ctt cct       195
Glu Asn Val Arg Ser Phe Phe Gln Ile Gly Gly Ile His Gly Leu Pro
                 50                  55                  60 tac act cct tgg gac ggt ata act ggt gat caa ccc ttc gac cca aac       243
Tyr Thr Pro Trp Asp Gly Ile Thr Gly Asp Gln Pro Phe Asp Pro Asn
                 65                  70                  75 act caa tgg gga ggg tac tgc act cat gga tcc gtt ctg ttc cct act       291
Thr Gln Trp Gly Gly Tyr Cys Thr His Gly Ser Val Leu Phe Pro Thr
                 80                  85                  90 tgg cac agg ccc tac gtt ctt ctc tac gag caa atc ctc cac aag cac       339
Trp His Arg Pro Tyr Val Leu Leu Tyr Glu Gln Ile Leu His Lys His
 95                 100                 105 gta cag gac atc gcc gcg act tac acc act tcc gat aag gcc gct tgg       387
Val Gln Asp Ile Ala Ala Thr Tyr Thr Thr Ser Asp Lys Ala Ala Trp
110                 115                 120                 125 gtg cag gct gct gct aat ctt cgt caa ccg tac tgg gat tgg gct gcg       435
Val Gln Ala Ala Ala Asn Leu Arg Gln Pro Tyr Trp Asp Trp Ala Ala
                130                 135                 140 aat gct gtt cct cct gac cag gtc atc gtg tcg aag aag gta acg atc       483
Asn Ala Val Pro Pro Asp Gln Val Ile Val Ser Lys Lys Val Thr Ile
                145                 150                 155 acc ggc tcc aac gga cac aaa gtc gag gtg gac aat cct ctg tac cat       531
Thr Gly Ser Asn Gly His Lys Val Glu Val Asp Asn Pro Leu Tyr His
                160                 165                 170 tac aag ttc cat ccg att gat tct tca ttc cct cgc cca tat tcc gag       579
Tyr Lys Phe His Pro Ile Asp Ser Ser Phe Pro Arg Pro Tyr Ser Glu
175                 180                 185 tgg ccg acc acc ctc agg caa cca aac agc tct cgg cca aat gct acg       627
Trp Pro Thr Thr Leu Arg Gln Pro Asn Ser Ser Arg Pro Asn Ala Thr
190                 195                 200                 205 gac aac gtc gca aag tta aga aac gtt ctt cgt gcg tcc cag gag aac       675
Asp Asn Val Ala Lys Leu Arg Asn Val Leu Arg Ala Ser Gln Glu Asn
                210                 215                 220 ata acg tct aac acg tat agc atg ctc acg cgt gta cat act tgg aag       723
Ile Thr Ser Asn Thr Tyr Ser Met Leu Thr Arg Val His Thr Trp Lys
                225                 230                 235 gcg ttc agt aac cac act gtt ggc gat ggt gga agc acc agt aac agt       771
Ala Phe Ser Asn His Thr Val Gly Asp Gly Gly Ser Thr Ser Asn Ser
                240                 245                 250 ctt gag gcc atc cac gat gga att cat gtt gat gtt gga gga gga gga       819
Leu Glu Ala Ile His Asp Gly Ile His Val Asp Val Gly Gly Gly Gly
255                 260                 265 cat atg ggt gat cct gct gtc gct gct ttc gat cct atc ttc ttc ttg       867
His Met Gly Asp Pro Ala Val Ala Ala Phe Asp Pro Ile Phe Phe Leu
270                 275                 280                 285 cat cac tgc aac gtc gat agg ctc ctc tct ctt tgg gcg gct att aac       915
His His Cys Asn Val Asp Arg Leu Leu Ser Leu Trp Ala Ala Ile Asn
                290                 295                 300 cct ggt gtc tgg gtc agc ccc gga gac tca gag gac ggg acc ttt atc       963
Pro Gly Val Trp Val Ser Pro Gly Asp Ser Glu Asp Gly Thr Phe Ile
```

-continued

```
                    305                     310                     315
ctt ccg cct gag gct ccc gtc gat gtt tcg act cct ctg acc ccg ttc      1011
Leu Pro Pro Glu Ala Pro Val Asp Val Ser Thr Pro Leu Thr Pro Phe
        320                     325                     330 tcc aac act gag act aca ttc tgg gct tct ggc ggc atc aca gac acc      1059
Ser Asn Thr Glu Thr Thr Phe Trp Ala Ser Gly Gly Ile Thr Asp Thr
            335                     340                     345 acc aaa ctt ggc tat act tac ccc gag ttc aac gga ctt gac ttg ggc      1107
Thr Lys Leu Gly Tyr Thr Tyr Pro Glu Phe Asn Gly Leu Asp Leu Gly
350                     355                     360                     365 aat gct caa gca gtc aaa gcg gcc att ggt aat atc gtc aac cgc ctg      1155
Asn Ala Gln Ala Val Lys Ala Ala Ile Gly Asn Ile Val Asn Arg Leu
                370                     375                     380 tac gga gct tcg gtt ttc agt ggg ttt gct gct gct acg tct gct ata      1203
Tyr Gly Ala Ser Val Phe Ser Gly Phe Ala Ala Ala Thr Ser Ala Ile
                    385                     390                     395 ggc gca ggg tcc gtg gct tcc ctg gca gca gat gtt ccg ttg gag aag      1251
Gly Ala Gly Ser Val Ala Ser Leu Ala Ala Asp Val Pro Leu Glu Lys
                        400                     405                     410 gcc cct gcc ccc gcc ccc gaa gcc gct gcc cag cct ccc gtc ccc gcc      1299
Ala Pro Ala Pro Ala Pro Glu Ala Ala Ala Gln Pro Pro Val Pro Ala
415                     420                     425 cct gct cat gtg gaa cca gcc gtt cgg gca gtt tct gtc cat gcc gct      1347
Pro Ala His Val Glu Pro Ala Val Arg Ala Val Ser Val His Ala Ala
430                     435                     440                     445 gct gcc cag ccc cat gcc gag cct cct gtt cat gtg tcc gct gga ggt      1395
Ala Ala Gln Pro His Ala Glu Pro Pro Val His Val Ser Ala Gly Gly
                450                     455                     460 cac ccg tct ccc cat ggg ttc tat gac tgg acc gcc cgt atc gaa ttc      1443
His Pro Ser Pro His Gly Phe Tyr Asp Trp Thr Ala Arg Ile Glu Phe
                    465                     470                     475 aag aaa tac gaa ttt ggg tct agc ttc tct gta ctc ctc ttc ctc ggc      1491
Lys Lys Tyr Glu Phe Gly Ser Ser Phe Ser Val Leu Leu Phe Leu Gly
                        480                     485                     490 ccc gtc cca gag gat ccc gaa caa tgg ctc gtc agt ccc aac ttc gtt      1539
Pro Val Pro Glu Asp Pro Glu Gln Trp Leu Val Ser Pro Asn Phe Val
495                     500                     505 ggc gcc cat cac gcc ttc gtc aac agc gcc gca ggg cac tgc gcc aac      1587
Gly Ala His His Ala Phe Val Asn Ser Ala Ala Gly His Cys Ala Asn
510                     515                     520                     525 tgt cgc agt caa ggc aat gta gtg gtc gaa ggc ttc gtc cat ctg act      1635
Cys Arg Ser Gln Gly Asn Val Val Val Glu Gly Phe Val His Leu Thr
                530                     535                     540 aaa tac att tct gag cat gct gga ttg cgc tcg tta aac ccc gaa gtt      1683
Lys Tyr Ile Ser Glu His Ala Gly Leu Arg Ser Leu Asn Pro Glu Val
                    545                     550                     555 gtc gag cca tat ctc act aat gaa ctt cat tgg aga gtg ttg aag gct      1731
Val Glu Pro Tyr Leu Thr Asn Glu Leu His Trp Arg Val Leu Lys Ala
                        560                     565                     570 gat gga tct gtg ggt caa ctt gaa tct ctt gaa gtt tcc gta tat ggc      1779
Asp Gly Ser Val Gly Gln Leu Glu Ser Leu Glu Val Ser Val Tyr Gly
575                     580                     585 acg cct atg aac ttg cct gtt ggt gcg atg ttc ccc gtc cct gga aat      1827
Thr Pro Met Asn Leu Pro Val Gly Ala Met Phe Pro Val Pro Gly Asn
590                     595                     600                     605 cgt cgt cac ttc cac ggc atc act cac ggg cgc gtc gga ggc agc cgt      1875
Arg Arg His Phe His Gly Ile Thr His Gly Arg Val Gly Gly Ser Arg
                610                     615                     620 cat gcc att gtt taa acgttggcac gttcatcaac gtcaattt                   1918
His Ala Ile Val
```

-continued

625

<210> SEQ ID NO 2
<211> LENGTH: 625
<212> TYPE: PRT
<213> ORGANISM: Pholiota nameko

<400> SEQUENCE: 2

```
Met Ser Arg Val Val Ile Thr Gly Val Ser Gly Thr Ile Ala Asn Arg
1               5                   10                  15

Leu Glu Ile Asn Asp Phe Val Lys Asn Asp Lys Phe Ser Leu Tyr
            20                  25                  30

Ile Gln Ala Leu Gln Val Met Ser Val Pro Pro Gln Glu Asn Val
            35                  40                  45

Arg Ser Phe Phe Gln Ile Gly Gly Ile His Gly Leu Pro Tyr Thr Pro
    50                  55                  60

Trp Asp Gly Ile Thr Gly Asp Gln Pro Phe Asp Pro Asn Thr Gln Trp
65                  70                  75                  80

Gly Gly Tyr Cys Thr His Gly Ser Val Leu Phe Pro Thr Trp His Arg
                85                  90                  95

Pro Tyr Val Leu Leu Tyr Glu Gln Ile Leu His Lys His Val Gln Asp
            100                 105                 110

Ile Ala Ala Thr Tyr Thr Thr Ser Asp Lys Ala Ala Trp Val Gln Ala
            115                 120                 125

Ala Ala Asn Leu Arg Gln Pro Tyr Trp Asp Trp Ala Ala Asn Ala Val
        130                 135                 140

Pro Pro Asp Gln Val Ile Val Ser Lys Lys Val Thr Ile Thr Gly Ser
145                 150                 155                 160

Asn Gly His Lys Val Glu Val Asp Asn Pro Leu Tyr His Tyr Lys Phe
                165                 170                 175

His Pro Ile Asp Ser Ser Phe Pro Arg Pro Tyr Ser Glu Trp Pro Thr
            180                 185                 190

Thr Leu Arg Gln Pro Asn Ser Ser Arg Pro Asn Ala Thr Asp Asn Val
        195                 200                 205

Ala Lys Leu Arg Asn Val Leu Arg Ala Ser Gln Glu Asn Ile Thr Ser
    210                 215                 220

Asn Thr Tyr Ser Met Leu Thr Arg Val His Thr Trp Lys Ala Phe Ser
225                 230                 235                 240

Asn His Thr Val Gly Asp Gly Ser Thr Ser Asn Ser Leu Glu Ala
                245                 250                 255

Ile His Asp Gly Ile His Val Asp Val Gly Gly Gly His Met Gly
            260                 265                 270

Asp Pro Ala Val Ala Ala Phe Asp Pro Ile Phe Leu His His Cys
        275                 280                 285

Asn Val Asp Arg Leu Leu Ser Leu Trp Ala Ala Ile Asn Pro Gly Val
    290                 295                 300

Trp Val Ser Pro Gly Asp Ser Glu Asp Gly Thr Phe Ile Leu Pro Pro
305                 310                 315                 320

Glu Ala Pro Val Asp Val Ser Thr Pro Leu Thr Pro Phe Ser Asn Thr
                325                 330                 335

Glu Thr Thr Phe Trp Ala Ser Gly Gly Ile Thr Asp Thr Lys Leu
            340                 345                 350

Gly Tyr Thr Tyr Pro Glu Phe Asn Gly Leu Asp Leu Gly Asn Ala Gln
        355                 360                 365

Ala Val Lys Ala Ala Ile Gly Asn Ile Val Asn Arg Leu Tyr Gly Ala
```

```
                370                 375                 380
Ser Val Phe Ser Gly Phe Ala Ala Thr Ser Ala Ile Gly Ala Gly
385                 390                 395                 400

Ser Val Ala Ser Leu Ala Ala Asp Val Pro Leu Glu Lys Ala Pro
                405                 410                 415

Pro Ala Pro Glu Ala Ala Gln Pro Val Pro Ala Pro Ala His
420                 425                 430

Val Glu Pro Ala Val Arg Ala Val Ser Val His Ala Ala Ala Gln
                435                 440                 445

Pro His Ala Glu Pro Val His Val Ser Ala Gly Gly His Pro Ser
            450                 455                 460

Pro His Gly Phe Tyr Asp Trp Thr Ala Arg Ile Glu Phe Lys Lys Tyr
465                 470                 475                 480

Glu Phe Gly Ser Ser Phe Ser Val Leu Leu Phe Leu Gly Pro Val Pro
                485                 490                 495

Glu Asp Pro Glu Gln Trp Leu Val Ser Pro Asn Phe Val Gly Ala His
            500                 505                 510

His Ala Phe Val Asn Ser Ala Ala Gly His Cys Ala Asn Cys Arg Ser
        515                 520                 525

Gln Gly Asn Val Val Glu Gly Phe Val His Leu Thr Lys Tyr Ile
    530                 535                 540

Ser Glu His Ala Gly Leu Arg Ser Leu Asn Pro Glu Val Glu Pro
545                 550                 555                 560

Tyr Leu Thr Asn Glu Leu His Trp Arg Val Leu Lys Ala Asp Gly Ser
                565                 570                 575

Val Gly Gln Leu Glu Ser Leu Glu Val Ser Val Tyr Gly Thr Pro Met
            580                 585                 590

Asn Leu Pro Val Gly Ala Met Phe Pro Val Pro Gly Asn Arg Arg His
        595                 600                 605

Phe His Gly Ile Thr His Gly Arg Val Gly Gly Ser Arg His Ala Ile
    610                 615                 620

Val
625

<210> SEQ ID NO 3
<211> LENGTH: 1918
<212> TYPE: DNA
<213> ORGANISM: Pholiota nameko
<220> FEATURE:
<221> NAME/KEY: CDS
<222> LOCATION: (13)..(1890)

<400> SEQUENCE: 3
ccactctgag aa atg tct cgc gtt gtt atc act ggt gtt tct ggc act gtc        51
              Met Ser Arg Val Val Ile Thr Gly Val Ser Gly Thr Val
                1               5                   10 gcc aat cgt ctc gaa atc aat gat ttc gtc aag aac gac aag ttt ttc         99
Ala Asn Arg Leu Glu Ile Asn Asp Phe Val Lys Asn Asp Lys Phe Phe
        15                  20                  25 tcg ctc tac att caa gct ctt cag gtt atg agc tca gtt cca cct cag       147
Ser Leu Tyr Ile Gln Ala Leu Gln Val Met Ser Ser Val Pro Pro Gln
30                  35                  40                  45 gaa aac gtc cga tcc ttc ttc cag atc gga ggt att cac ggc ctt cct       195
Glu Asn Val Arg Ser Phe Phe Gln Ile Gly Gly Ile His Gly Leu Pro
                50                  55                  60 tac act cct tgg gac ggt ata act ggt gat caa ccc ttc gac cca aac       243
Tyr Thr Pro Trp Asp Gly Ile Thr Gly Asp Gln Pro Phe Asp Pro Asn
            65                  70                  75
```

```
act caa tgg gga ggg tac tgc act cat gga tcc gtt ctg ttc cct act    291
Thr Gln Trp Gly Gly Tyr Cys Thr His Gly Ser Val Leu Phe Pro Thr
         80                  85                  90 tgg cac agg ccc tac gtt ctt ctc tac gag caa atc ctc cac aag cac    339
Trp His Arg Pro Tyr Val Leu Leu Tyr Glu Gln Ile Leu His Lys His
 95                 100                 105 gta cag gac atc gcc gcg act tac acc act tcc gat aag gcc gct tgg    387
Val Gln Asp Ile Ala Ala Thr Tyr Thr Thr Ser Asp Lys Ala Ala Trp
110                 115                 120                 125 gtg cag gct gct gct aat ctt cgt caa ccg tac tgg gat tgg gct gcg    435
Val Gln Ala Ala Ala Asn Leu Arg Gln Pro Tyr Trp Asp Trp Ala Ala
                130                 135                 140 aat gct gtt cct cct gac cag gtc atc gcg tcg aag aag gta acg atc    483
Asn Ala Val Pro Pro Asp Gln Val Ile Ala Ser Lys Lys Val Thr Ile
                145                 150                 155 acc ggc tcc aac gga cac aaa gtc gag gtg gac aat cct ctg tac cat    531
Thr Gly Ser Asn Gly His Lys Val Glu Val Asp Asn Pro Leu Tyr His
                160                 165                 170 tac aag ttc cat ccg att gat tct tca ttc cct cgc cca tat tcc gag    579
Tyr Lys Phe His Pro Ile Asp Ser Ser Phe Pro Arg Pro Tyr Ser Glu
175                 180                 185 tgg ccg acc acc ctc agg caa cca aac agc tct cgg cca aat gct acg    627
Trp Pro Thr Thr Leu Arg Gln Pro Asn Ser Ser Arg Pro Asn Ala Thr
190                 195                 200                 205 gac aac gtc gca aag tta aga aac gtt ctt cgt gcg tcc cag gag aac    675
Asp Asn Val Ala Lys Leu Arg Asn Val Leu Arg Ala Ser Gln Glu Asn
                210                 215                 220 ata acg tct aac acg tat agc atg ctc acg cgt gta cat act tgg aag    723
Ile Thr Ser Asn Thr Tyr Ser Met Leu Thr Arg Val His Thr Trp Lys
                225                 230                 235 gcg ttc agt aac cac act gtt ggc gat ggt gga agc acc agt aac agt    771
Ala Phe Ser Asn His Thr Val Gly Asp Gly Gly Ser Thr Ser Asn Ser
                240                 245                 250 ctc gag gcc atc cac gat gga att cat gtt gat gtt gga gga gga gga    819
Leu Glu Ala Ile His Asp Gly Ile His Val Asp Val Gly Gly Gly Gly
                255                 260                 265 cat atg gct gat cct gct gtc gct gct ttc gat cct atc ttc ttc ttg    867
His Met Ala Asp Pro Ala Val Ala Ala Phe Asp Pro Ile Phe Phe Leu
270                 275                 280                 285 cat cac tgc aac gtc gat agg ctc ctc tct ctt tgg gcg gct att aac    915
His His Cys Asn Val Asp Arg Leu Leu Ser Leu Trp Ala Ala Ile Asn
                290                 295                 300 cct ggt gtc tgg gtc agc ccc gga gac tca gag gac ggg acc ttt atc    963
Pro Gly Val Trp Val Ser Pro Gly Asp Ser Glu Asp Gly Thr Phe Ile
                305                 310                 315 ctt ccg cct gag gct ccc gtc gat gtt tcg act cct ctg acc ccg ttc   1011
Leu Pro Pro Glu Ala Pro Val Asp Val Ser Thr Pro Leu Thr Pro Phe
                320                 325                 330 tcc aac act gag act aca ttc tgg gct tct ggc ggc atc aca gac acc   1059
Ser Asn Thr Glu Thr Thr Phe Trp Ala Ser Gly Gly Ile Thr Asp Thr
335                 340                 345 acc aaa ctt ggc tat act tac ccc gag ttc aac gga ctt gac ttg ggc   1107
Thr Lys Leu Gly Tyr Thr Tyr Pro Glu Phe Asn Gly Leu Asp Leu Gly
350                 355                 360                 365 aat gct caa gca gtc aaa gcg gcc att ggt aat atc gtc aac cgc ctg   1155
Asn Ala Gln Ala Val Lys Ala Ala Ile Gly Asn Ile Val Asn Arg Leu
                370                 375                 380 tac gga gct tcg gtt ttc agt ggg ttt gct gcc gct acg tct gct ata   1203
Tyr Gly Ala Ser Val Phe Ser Gly Phe Ala Ala Ala Thr Ser Ala Ile
                385                 390                 395
```

```
ggc gca ggg tcc gtg gct tcc ctg gca gca gat gtt ccg ttg gag aag    1251
Gly Ala Gly Ser Val Ala Ser Leu Ala Ala Asp Val Pro Leu Glu Lys
        400                 405                 410 gcc cct gcc ccc gcc ccc gaa gcc gct gcc cag tct ccc gtc ccc gcc    1299
Ala Pro Ala Pro Ala Pro Glu Ala Ala Ala Gln Ser Pro Val Pro Ala
415                 420                 425 cct gct cat gtt gaa cca gcc gtt cgg gca gtt tct gtc cat gcc gct    1347
Pro Ala His Val Glu Pro Ala Val Arg Ala Val Ser Val His Ala Ala
430                 435                 440                 445 gct gcc cag ccc cat gcc gag cct cct gtt cat gtg tcc gct gga ggt    1395
Ala Ala Gln Pro His Ala Glu Pro Pro Val His Val Ser Ala Gly Gly
            450                 455                 460 cac ccg tct ccc cac ggg ttc tat gac tgg acc gcc cgt atc gaa ttc    1443
His Pro Ser Pro His Gly Phe Tyr Asp Trp Thr Ala Arg Ile Glu Phe
        465                 470                 475 aag aaa tac gaa ttt ggg tct agc ttc tct gta ctc ctc ttc ctc ggc    1491
Lys Lys Tyr Glu Phe Gly Ser Ser Phe Ser Val Leu Leu Phe Leu Gly
    480                 485                 490 ccc gtc cca gag gat ccc gaa caa tgg ctc gtc agt ccc aac ttc gtg    1539
Pro Val Pro Glu Asp Pro Glu Gln Trp Leu Val Ser Pro Asn Phe Val
495                 500                 505 ggc gcc cat cac gcc ttc gtc aac agc gcc gca ggg cac tgc gcc aac    1587
Gly Ala His His Ala Phe Val Asn Ser Ala Ala Gly His Cys Ala Asn
510                 515                 520                 525 tgt cgc aat caa ggc aat gta gtg gtc gaa ggc ttc gtc cat ctg act    1635
Cys Arg Asn Gln Gly Asn Val Val Val Glu Gly Phe Val His Leu Thr
            530                 535                 540 aaa tac att tct gag cat gct gga ttg cgc tcg tta aac ccc gaa gtt    1683
Lys Tyr Ile Ser Glu His Ala Gly Leu Arg Ser Leu Asn Pro Glu Val
        545                 550                 555 gtc gag cca tat ctt act aat gaa ctt cat tgg aga gtg ttg aag gct    1731
Val Glu Pro Tyr Leu Thr Asn Glu Leu His Trp Arg Val Leu Lys Ala
    560                 565                 570 gat gga tct gtg ggt caa ctt gaa tct ctt gaa gtt tcc gta tat ggc    1779
Asp Gly Ser Val Gly Gln Leu Glu Ser Leu Glu Val Ser Val Tyr Gly
575                 580                 585 acg cct atg aac ttg cct gtt ggt gcg atg ttc ccc gtc cct gga aat    1827
Thr Pro Met Asn Leu Pro Val Gly Ala Met Phe Pro Val Pro Gly Asn
590                 595                 600                 605 cgt cgt cac ttc cac ggc atc act cac ggg cgc gtc gga ggc agc cgt    1875
Arg Arg His Phe His Gly Ile Thr His Gly Arg Val Gly Gly Ser Arg
            610                 615                 620 cat gcc att gtt taa acgttggcac gttcatcaac gtcaattt                 1918
His Ala Ile Val
            625

<210> SEQ ID NO 4
<211> LENGTH: 625
<212> TYPE: PRT
<213> ORGANISM: Pholiota nameko

<400> SEQUENCE: 4

Met Ser Arg Val Val Ile Thr Gly Val Ser Gly Thr Ala Asn Arg
1               5                   10                  15

Leu Glu Ile Asn Asp Phe Val Lys Asn Asp Lys Phe Phe Ser Leu Tyr
            20                  25                  30

Ile Gln Ala Leu Gln Val Met Ser Ser Val Pro Pro Gln Glu Asn Val
        35                  40                  45

Arg Ser Phe Phe Gln Ile Gly Gly Ile His Gly Leu Pro Tyr Thr Pro
    50                  55                  60
```

-continued

```
Trp Asp Gly Ile Thr Gly Asp Gln Pro Phe Asp Pro Asn Thr Gln Trp
 65                  70                  75                  80

Gly Gly Tyr Cys Thr His Gly Ser Val Leu Phe Pro Thr Trp His Arg
                 85                  90                  95

Pro Tyr Val Leu Leu Tyr Glu Gln Ile Leu His Lys His Val Gln Asp
            100                 105                 110

Ile Ala Ala Thr Tyr Thr Thr Ser Asp Lys Ala Ala Trp Val Gln Ala
        115                 120                 125

Ala Ala Asn Leu Arg Gln Pro Tyr Trp Asp Trp Ala Ala Asn Ala Val
    130                 135                 140

Pro Pro Asp Gln Val Ile Ala Ser Lys Lys Val Thr Ile Thr Gly Ser
145                 150                 155                 160

Asn Gly His Lys Val Glu Val Asp Asn Pro Leu Tyr His Tyr Lys Phe
                165                 170                 175

His Pro Ile Asp Ser Ser Phe Pro Arg Pro Tyr Ser Glu Trp Pro Thr
            180                 185                 190

Thr Leu Arg Gln Pro Asn Ser Ser Arg Pro Asn Ala Thr Asp Asn Val
        195                 200                 205

Ala Lys Leu Arg Asn Val Leu Arg Ala Ser Gln Glu Asn Ile Thr Ser
    210                 215                 220

Asn Thr Tyr Ser Met Leu Thr Arg Val His Thr Trp Lys Ala Phe Ser
225                 230                 235                 240

Asn His Thr Val Gly Asp Gly Ser Thr Ser Asn Ser Leu Glu Ala
                245                 250                 255

Ile His Asp Gly Ile His Val Asp Val Gly Gly Gly His Met Ala
            260                 265                 270

Asp Pro Ala Val Ala Ala Phe Asp Pro Ile Phe Leu His His Cys
        275                 280                 285

Asn Val Asp Arg Leu Leu Ser Leu Trp Ala Ala Ile Asn Pro Gly Val
290                 295                 300

Trp Val Ser Pro Gly Asp Ser Glu Asp Gly Thr Phe Ile Leu Pro Pro
305                 310                 315                 320

Glu Ala Pro Val Asp Val Ser Thr Pro Leu Thr Pro Phe Ser Asn Thr
                325                 330                 335

Glu Thr Thr Phe Trp Ala Ser Gly Gly Ile Thr Asp Thr Thr Lys Leu
            340                 345                 350

Gly Tyr Thr Tyr Pro Glu Phe Asn Gly Leu Asp Leu Gly Asn Ala Gln
        355                 360                 365

Ala Val Lys Ala Ala Ile Gly Asn Ile Val Asn Arg Leu Tyr Gly Ala
    370                 375                 380

Ser Val Phe Ser Gly Phe Ala Ala Thr Ser Ala Ile Gly Ala Gly
385                 390                 395                 400

Ser Val Ala Ser Leu Ala Ala Asp Val Pro Leu Glu Lys Ala Pro Ala
                405                 410                 415

Pro Ala Pro Glu Ala Ala Ala Gln Ser Pro Val Pro Ala Pro Ala His
            420                 425                 430

Val Glu Pro Ala Val Arg Ala Val Ser Val His Ala Ala Ala Ala Gln
        435                 440                 445

Pro His Ala Glu Pro Val His Val Ser Ala Gly Gly His Pro Ser
    450                 455                 460

Pro His Gly Phe Tyr Asp Trp Thr Ala Arg Ile Glu Phe Lys Lys Tyr
465                 470                 475                 480

Glu Phe Gly Ser Ser Phe Ser Val Leu Leu Phe Leu Gly Pro Val Pro
```

-continued

```
                            485                 490                 495
Glu Asp Pro Glu Gln Trp Leu Val Ser Pro Asn Phe Val Gly Ala His
            500                 505                 510

His Ala Phe Val Asn Ser Ala Ala Gly His Cys Ala Asn Cys Arg Asn
            515                 520                 525

Gln Gly Asn Val Val Val Glu Gly Phe Val His Leu Thr Lys Tyr Ile
            530                 535                 540

Ser Glu His Ala Gly Leu Arg Ser Leu Asn Pro Glu Val Val Glu Pro
545                 550                 555                 560

Tyr Leu Thr Asn Glu Leu His Trp Arg Val Leu Lys Ala Asp Gly Ser
                565                 570                 575

Val Gly Gln Leu Glu Ser Leu Glu Val Ser Val Tyr Gly Thr Pro Met
            580                 585                 590

Asn Leu Pro Val Gly Ala Met Phe Pro Val Pro Gly Asn Arg Arg His
            595                 600                 605

Phe His Gly Ile Thr His Gly Arg Val Gly Gly Ser Arg His Ala Ile
            610                 615                 620

Val
625

<210> SEQ ID NO 5
<211> LENGTH: 4
<212> TYPE: PRT
<213> ORGANISM: Artificial Sequence
<220> FEATURE:
<223> OTHER INFORMATION: substrate peptide

<400> SEQUENCE: 5

Gly Gly Tyr Arg
1
```

COLOR REACTION USING TYROSINASE AND PEPTIDE

TECHNICAL FIELD

The present invention relates to a color reaction using tyrosinase and peptide.

BACKGROUND ART

Tyrosinase is an enzyme that is also referred to as monophenol monooxygenase or catechol oxidase. Tyrosinase catalyzes an oxidation reaction of phenols.

Oxidization and polymerization of tyrosine allows tyrosinase to synthesize melanin, thus presenting a color ranging from brown to black.

A melanin precursor, which is obtained by using DOPA or dopamine as a substrate, also becomes a black melanin by polymerization. In addition, while a melanin precursor obtained by using α-alkyl ester of tyrosine or α-alkyl ester of DOPA as a substrate will become a black melanin by polymerization, the polymerization of the melanin precursor with an adjustment of pH will allow for synthesis of melanin in a color ranging from yellow to purple. Furthermore, a melanin precursor, which is obtained by using tyrosine or DOPA together with cysteine as a substrate, will become brown melanin (Non-patent documents 1 and 2).

In conventional methods as described above, it was necessary to adjust the pH of enzyme reactions for coloration of colors other than brown to black. Furthermore, even if the pH of enzyme reactions is adjusted, it was not possible to perform coloration of bright green to blue colors.

Tyrosinase is originally associated with reactions for change in colors such as black, red-brown, yellow-brown, purple and dark purple, and thus tyrosinase has not been preferably used for food or the like. However, if a coloration substance of a bright color, ranging from blue to green, can be prepared by tyrosinase, the substance can be applied to food or the like.

PRIOR ART DOCUMENTS

Patent Documents

Patent Document 1: Japanese Laid-Open Publication No. 2006-158304

Patent Document 1: Japanese Laid-Open Publication No. 2010-115213

SUMMARY OF INVENTION

Problem to be Solved by the Invention

Thus, there is a need for development of color reactions for easily coloring bright green to blue colors by using tyrosinase.

Means for Solving the Problem

The present inventors unexpectedly developed a color reaction for easy coloration of bright green to blue colors by allowing a short peptide (typically trimer or tetramer) to react with tyrosinase, thus completing the present invention.

For example, the following are provided by the present invention:

(Item 1)
A coloration method comprising the steps of:
(a) mixing peptide and tyrosinase;
(b) incubating the mixture; and
(d) cryopreserving the incubated mixture.

(Item 2)
The coloration method according to Item 1, wherein the length of the peptide ranges from dimer to pentamer.

(Item 3)
The coloration method according to Item 1, wherein the length of the peptide ranges from trimer to tetramer.

(Item 4)
The coloration method according to Item 1, wherein the cryopreserving is performed at a temperature ranging from −80° C. to 0° C.

(Item 5)
The coloration method according to Item 1, wherein the cryopreserving is performed at a temperature ranging from −40° C. to −20° C.

(Item 6)
The coloration method according to Item 1, wherein the cryopreserving is performed at a temperature of −30° C.

(Item 7)
The coloration method according to Item 1, wherein at step (a), amino acid is further mixed.

(Item 8)
The coloration method according to Item 1, wherein at step (a), glycine is further mixed.

(Item 9)
The coloration method according to Item 1, further comprising a step (c), after step (b) and before step (d), adjusting the pH of the mixture.

(Item 10)
The coloration method according to Item 9, wherein the pH at step (c) ranges from 8 to 11.

(Item 11)
The coloration method according to Item 1, wherein the tyrosinase is derived from *Pholiota nameko*.

(Item 12)
The coloration method according to Item 11, wherein the tyrosinase derived from *Pholiota nameko* is encoded by a polynucleotide selected from the group consisting of:
(1) a polypeptide comprising a base sequence set forth in SEQ ID NO: 1 or 3, or a fragment sequence thereof;
(2) a polynucleotide comprising a sequence encoding an amino acid sequence set forth in SEQ ID NO: 2 or 4, or a fragment thereof;
(3) a polynucleotide encoding a variant polypeptide, in which one or more amino acids have at least one mutation selected from the group consisting of substitution, addition and deletion, in an amino acid sequence set forth in SEQ ID NO: 2 or 4;
(4) a polynucleotide hybridizing to a complementary strand of any one of the polynucleotides (1) to (3) under stringent conditions; and
(5) a polynucleotide consisting of a base sequence having at least 70% identity to any one of the polynucleotides (1) to (3) or a complementary sequence thereof, and has tyrosinase activity.

(Item 13)
The coloration method according to Item 11, wherein the tyrosinase derived from *Pholiota nameko* is encoded by a polynucleotide selected from the group consisting of:

(6) a polynucleotide consisting of a base sequence set forth in SEQ ID NO: 1 or 3; and
(7) a polynucleotide consisting of an amino acid sequence set forth in SEQ ID NO: 2 or 4.
(Item 14)
The coloration method according to Item 1, wherein: the peptide is a peptide in which an N terminus is modified; and amino acid is further mixed at step (a).
(Item 15)
The coloration method according to Item 1, wherein: the peptide is a peptide in which an N terminus is modified; and glycine is further mixed at step (a).
(Item 16)
The coloration method according to Item 14 or 15, wherein modification of the N terminus is acetylation of an amino group of the N terminus.
(Item 17)
A kit for performing a color reaction, comprising:
(i) peptide; and
(ii) tyrosinase.
(Item 18)
The kit according to Item 17, wherein the length of the peptide ranges from dimer to pentamer.
(Item 19)
The kit according to Item 17, wherein the length of the peptide ranges from trimer to tetramer.
(Item 20)
The kit according to Item 17, further comprising amino acid.
(Item 21)
The kit according to Item 17, further comprising glycine.
(Item 22)
The kit according to Item 17, wherein the tyrosinase is derived from *Pholiota nameko*.
(Item 23)
The kit according to Item 22, wherein the tyrosinase derived from *Pholiota nameko* is encoded by a polynucleotide selected from the group consisting of:
(1) a polypeptide comprising a base sequence set forth in SEQ ID NO: 1 or 3, or a fragment sequence thereof;
(2) a polynucleotide comprising a sequence encoding an amino acid sequence set forth in SEQ ID NO: 2 or 4, or a fragment thereof;
(3) a polynucleotide encoding a variant polypeptide, in which one or more amino acids have at least one mutation selected from the group consisting of substitution, addition and deletion, in an amino acid sequence set forth in SEQ ID NO: 2 or 4;
(4) a polynucleotide hybridizing to a complementary strand of any one of the polynucleotides (1) to (3) under stringent conditions; and
(5) a polynucleotide consisting of a base sequence having at least 70% identity to any one of the polynucleotides (1) to (3) or a complementary sequence thereof, and has tyrosinase activity.
(Item 24)
The kit according to Item 22, wherein the tyrosinase derived from *Pholiota nameko* is encoded by a polynucleotide selected from the group consisting of:
(6) a polynucleotide consisting of a base sequence set forth in SEQ ID NO: 1 or 3; and
(7) a polynucleotide consisting of an amino acid sequence set forth in SEQ ID NO: 2 or 4.
(Item 25)
The kit according to Item 17, wherein: the peptide is a peptide in which an N terminus is modified; and the kit further comprises (iv) amino acid.

(Item 26)
The kit according to Item 17, wherein: the peptide is a peptide in which an N terminus is modified; and the kit further comprises (iv) glycine.
(Item 27)
A product obtained by the coloration method according to Item 1.

Effect of the Invention

The present invention allows a color reaction to be performed easily for coloration of bright green to blue colors by using tyrosinase.

EMBODIMENTS FOR CARRYING OUT THE INVENTION

I. Definition of Terms

It should be understood that the terms as used herein have definitions typically used in the art unless otherwise mentioned. Thus, unless otherwise defined, all scientific and technical terms have the same meanings as those generally used by those skilled in the art to which the present invention pertains. If there is contradiction, the present specification (including the definition) controls.

Hereinafter, the present invention will be described by way of embodiments. Embodiments described below are provided only for illustrative purposes. Accordingly, the scope of the present invention is not limited by the embodiments except as by the claims. It will be clearly appreciated by those skilled in the art that variations and modifications can be made without departing from the scope of the present invention with reference to the specification.

As used herein, an amino acid sequence of a "peptide" may be an unmodified natural amino acid, or a modified amino acid. Amino acid modifications include, but are not limited to, amidation, carboxylation, sulfation, halogenation, truncation, lipidation, phosphorylation, alkylation, glycosylation, hydroxylation, and acylation (e.g., acetylation). Preferably, an amino group of an amino terminal of peptide is acylated.

As long as tyrosinase works, a "peptide analog" or a "peptide derivative" may be used instead of peptide. As used herein, the term "peptide analog" or "peptide derivative" refers to a compound that is different from peptide, but has at least one chemical function or biological function equivalent to that of the peptide. Thus, peptide analog includes those in which one or more amino acid analogs or amino acid derivatives are added or substituted, compared to the original peptide. Such an addition or substitution is made to the peptide analog in such a manner that its function is substantially the same as that of the original peptide (e.g., having similar pKa values, similar functional groups, similar binding modes with other molecules, similar water solubility, or the like). Such a peptide analog can be prepared using a well known technique in the art. Thus, the peptide analog can be an oligomer or polymer which includes an amino acid analog.

The peptides as used herein span from dimer to pentamer, and preferably trimer to tetramer. The peptides as used herein preferably include at least one tyrosine.

As used herein, the term "tyrosinase" is an enzyme that is also referred to as monophenol monooxygenase, or catechol oxygenase. Tyrosinase catalyzes an oxidation reaction of phenols. For example, tyrosinase catalyzes a reaction: L-tyrosine+L-dopa+$O_2$→L-dopa-dopaquinone+$H_2O$. Thus, tyrosinase oxygenizes tyrosine to produce melanin. There is no particular restriction to a method for measuring tyrosinase activity, and it can be measured using a normal method. The sources of supply of tyrosinase typically include, but are not limited to, *Pholiota nameko*, filamentous fungi, bacteria, plants and animals.

The "*Pholiota nameko*" used as a source for supplying "tyrosinase" herein include, but are not limited to, Pholiota microspora (Fungi, Basidiomycota, Hymenomycetes, Agaricales, Strophariaceae, Pholiota squarrosa, and *Pholiota nameko*). As used herein, the term, "tyrosinase derived from *Pholiota nameko*", refers to tyrosinase isolated from "*Pholiota nameko*" or tyrosinase encoded by the genome of *Pholiota nameko*. The "tyrosinase derived from *Pholiota nameko*" refers to a polypeptide encoded by a base sequence set forth in SEQ ID NO: 1 or a variant thereof, or a polypeptide comprising an amino acid sequence set forth in SEQ ID NO: 2 or a variant thereof. For example, such polypeptides include, but not limited to, a polypeptide encoded by a polynucleotide selected from the group consisting of:

(1) a polypeptide comprising a base sequence set forth in SEQ ID NO: 1 or a fragment sequence thereof;
(2) a polynucleotide comprising a sequence encoding an amino acid sequence set forth in SEQ ID NO: 2 or a fragment thereof;
(3) a polynucleotide encoding a variant polypeptide, in which one or more amino acids have at least one mutation selected from the group consisting of substitution, addition and deletion, in an amino acid sequence set forth in SEQ ID NO: 2;
(4) a polynucleotide hybridizing to a complementary strand of any one of the polynucleotides (1) to (3) under stringent conditions; and
(5) a polynucleotide consisting of a base sequence having at least 70%, 80%, 90%, 95%, 96%, 97%, 98% or 99% identity to any one of the polynucleotides (1) to (3) or a complementary sequence thereof,
and having tyrosinase activity.

As used herein, the term "homology" of a gene (e.g., a nucleic acid sequence, an amino acid sequence and the like) refers to the proportion of identity between two or more gene sequences. In addition, sequence identity (of a nucleic acid sequence, an amino acid sequence or the like) herein refers to the proportion of the identical sequence (individual nucleic acids, amino acids or the like) of two or more comparative sequences to each other. Therefore, the greater the homology between two given genes, the greater the identity or similarity between their sequences. Whether or not two genes have homology is determined by comparing their sequences directly or by a hybridization method under stringent conditions. When two gene sequences are directly compared with each other, these genes have homology if the DNA sequences of the genes have representatively at least 50% identity, preferably at least 70% identity, more preferably at least 80%, 90%, 95%, 96%, 97%, 98%, or 99% identity with each other. The "similarity" of gene (e.g., a nucleic acid sequence, an amino acid sequence or the like) herein refers to the proportion of identity of two or more gene sequences to each other when a conservative substitution is regarded as being positive (identical) in the above-mentioned homology. Therefore, when there is a conservative substitution, the homology and similarity are different from each other in accordance with the presence of the conservative substitution. In addition, when there is no conservative substitution, the homology and similarity indicate the same numerical value.

Herein, the comparison of amino acid sequences and base sequences in their similarity, identity and homology is made using a sequence analysis tool, FASTA, and is calculated using default parameters.

As used herein, the term "fragment" refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more nucleotides. Lengths represented by integers which are not herein specified (e.g., 11 and the like) may be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 11 and the like) may be appropriate as a lower limit. Herein, while the length of a polypeptide and a polynucleotide can be represented by the number of amino acids or nucleic acid respectively as described above, the above-described numbers are not absolute ones. The above-described numbers for upper limit and lower limit are not to be limiting but instead inclusive of a broader range (for example, 10% greater or less than), if the polypeptide and polynucleotide have the same function; furthermore, when the polypeptide and polynucleotide have the same function such polypeptides and poly nucleotides are to be included in the definition of fragment regardless the fragment length. Herein, in order to express such an intention, numbers may be expressed with a term "about" added thereto. However, it should be understood herein that the presence or absence of the term, "about", does not influence the interpretation of the numerical value. The length of a useful fragment herein can be determined by whether or not at least one of the functions of a full length protein, as a reference of the fragment, is retained.

Herein, "polynucleotide hybridizing under stringent conditions" refers to well known conditions commonly practiced in the art. Such a polynucleotide can be obtained with a polynucleotide selected from the polynucleotides of the present invention, as a probe, and using a colony hybridization technique, a plaque hybridization technique, Southern blot hybridization technique or the like. Specifically, such a polynucleotide is meant to be one that can be identified by performing hybridization at 65° C. under the presence of 0.7-1.0 M of NaCl using a filter on which DNA from a colony or plaque is immobilized, and then washing the filter under the 65° C. condition using 0.1-2 fold concentrations of a SSC (saline-sodium citrate) solution (where the composition of the 1 fold concentration of the SSC solution is 150 mM sodium chloride and 15 mM sodium citrate). Hybridization can be performed according to a method described in laboratory manuals such as Molecular Cloning 2nd ed., Current Protocols in Molecular Biology, Supplement 1-38, DNA Cloning 1: Core Techniques, A Practical Approach, Second Edition, Oxford University Press (1995). Herein, sequences comprising only an A sequence or a T sequence are preferably excluded from sequences hybridizing under stringent conditions. A "hybridizable polynucleotide" refers to a polynucleotide capable of hybridizing to another polynucleotide under the above-mentioned hybridizing conditions. Specifically, such a hybridizable polynucleotide includes a polynucleotide having at least 60% or more homology, preferably 80% or more homology, and still preferably 95% or more homology to a base sequence of DNA encoding a polypeptide having the amino acid sequence specifically indicated in the present invention.

As used herein, "highly stringent condition" refers to a condition designed to enable hybridization of a DNA chain having high complementarity in a nucleic acid sequence, and to exclude hybridization of DNA that has a significant mismatch. The stringency of hybridization is mainly determined by conditions such as temperature, ion strength, and a denaturing agent such as formamide. An example of a "highly stringent condition" related to such hybridization and washing is 0.0015M sodium chloride, 0.0015M sodium citrate, 65-68° C. (preferably, 65° C.), or 0.0015M sodium chloride, 0.0015M sodium citrate, and 50% formamide, and 42° C. For such a highly stringent condition, see Sambrook et al., Molecular Cloning: A Laboratory Manual, second edition, Cold Spring Harbor Laboratory (Cold Spring Harbor, N.Y. 1989); and Anderson et al., Nucleic Acid Hybridization: a Practical approach, IV, IRL Press Limited (Oxford, England). Limited, Oxford, England. As needs arise, a more stringent condition (e.g., higher temperature, lower ion strength, higher formamide, or other denaturating agent) may be used. Other agents can be comprised in a hybridization buffer solution and a wash buffer solution for the purpose of reducing non-specific hybridization and/or background hybridization. Examples of such other agents include 0.1% bovine serum albumin, 0.1% polyvinylpyrrolidone, 0.1% sodium pyrophosphate, 0.1% sodium dodecyl sulfate ($NaDodSO_4$ or SDS), Ficoll, Denhardt solution, sonicated salmon sperm DNA (or other non-complementary DNA), and dextran sulfate; however, other appropriate agents can also be used. The concentration and type of those additives can be varied without substantial influence on the stringency of the hybridization conditions. While hybridization experiments are normally performed at pH 6.8 to 7.4 (preferably, pH 7.0), the rate of hybridization is almost pH independent in representative ion strength conditions. See Anderson et al., Nucleic Acid Hybridization: a Practical Approach, Chapter 4, IRL Press Limited (Oxford, England).

Factors influencing the stability of DNA double strands include the compositions and length of a base sequence, and the degree of base pair mismatch. The hybridization conditions can be adjusted by those skilled in the art, and these variables are applied to allow DNA of different sequence relatedness to form a hybrid. The fusion temperature of completely matched DNA double strands can be roughly calculated by the following formula:

$$Tm(°C.) = 81.5 + 16.6(\log[Na^+]) + 0.41(\% G+C) - 600/N - 0.72(\% \text{ formamide})$$

wherein N is the length of a double strands to be formed; [$Na^+$] is the mol concentration of sodium ions in a hybridization solution or a wash solution; and % G+C is the percentage of a (guanine+cytosine) base in a hybrid. With regard to an incompletely matched hybrid, the fusion temperature is decreased by about 1° C. per 1% mismatch.

Herein, the percentage of the "identity", "homology" and "similarity" of a sequence (amino acid, nucleic acid and the like) is determined by comparing two sequences which are aligned in an optimal state in a comparison window. In comparison with a standard sequence for the optimum alignment of two sequences (it is assumed that although gaps may be generated when additions are contained in another sequence, the standard sequence herein does not have additions or deletions), additions or deletions (that is, gaps) can be included in the comparison window of polynucleotide sequences or polypeptide sequences. By determining the number of positions at which the same nucleic acid base or amino acid residue is recognized in both the sequences, the number of matched positions is determined, and the number of matched positions is divided by the number of positions in total in the comparison window and then multiplied by 100 to determine percentage identity. When used in a search, a suitable sequence comparison algorithm and program are selected from those well-known in the art, in order to evaluate homology. Such algorithms and programs include, but are not limited to, TBLASTN, BLASTP, FASTA, TFASTA and CLUSTALW (Pearson and Lipman, 1988, Proc. Natl. Acad. Sci. USA 85(8): 2444-2448, Altschul et al., 1990, J. Mol. Biol. 215(3): 403-410, Thompson et al., 1994, Nucleic Acids Res. 22(2): 4673-4680, Higgins et al., 1996, Methods Enzymol. 266: 383-402, Altschul et al., 1990, J. Mol. Biol. 215(3): 403-410, Altschul et al., 1993, Nature Genetics 3:266-272). In a particularly preferable embodiment, the homology between protein sequences or nucleic acid sequences is evaluated by using Basic Local Alignment Search Tool (BLAST) as well known in the art (see, for example, Karlin and Altschul, 1990, Proc. Natl. Acad. Sci. USA 87: 2267-2268, Altschul et al., 1990, J. Mol. Biol. 215:403-410, Altschul et al., 1993, Nature Genetics 3:266-272, Altschul et al., 1997, Nuc. Acids Res. 25:3389-3402). Particularly, comparison or search can be achieved by using five special BLAST programs and performing the following operations.

(1) comparison, by BLASTP and BLAST3, of an amino acid query sequence with a protein sequence database;

(2) comparison, by BLASTN, of a nucleotide query sequence with a nucleotide sequence database;

(3) comparison, by BLASTX, of a conceptual translation product into which the nucleotide query sequence (both strands) was converted in 6 reading frames, with a protein sequence database;

(4) comparison, by TBLASTN, of the protein query sequence with a database of nucleotide sequences converted in all 6 reading frames (both strands); and (5) comparison, by TBLASTX, of the nucleotide query sequence converted in 6 reading frames, with a database of nucleotide sequences converted in 6 reading frames.

The BLAST program is a program for identifying a homologous sequence by specifying a similar segment referred to as a "high-score segment pair" between an amino acid query sequence or a nucleic acid query sequence and a subject sequence, obtained preferably from a protein sequence database or a nucleic acid sequence database. Preferably, the high-score segment pair is identified (that is, aligned) by scoring matrices, many of which are well-known in the art. Preferably, BLOSUM62 matrix (Gonnet et al., 1992, Science 256: 1443-1445, Henikoff and Henikoff, 1993, Proteins 17:49-61) is used as the scoring matrix. Although not as preferable as the above-mentioned matrix, PAM or PAM250 matrix can also be used (see, for example, Schwartz and Dayhoff, eds., 1978, Matrices for Detecting Distance Relationships: Atlas of Protein Sequence and Structure, Washington: National Biochemical Research Foundation).

By using the BLAST program, the statistical significance of every identified high-score segment pair is evaluated to select preferably a segment satisfying a threshold level of significance established individually by the user, such as the degree of homology unique to the user. The statistical significance of the high-score segment pair is evaluated preferably using a Karlin formula for determining statistical significance (see Karlin and Altschul, 1990, Proc. Natl. Acad. Sci. USA 87:2267-2268).

(Modification of Genes, Protein Molecules, Nucleic Acid Molecules and the Like)

In a certain protein molecule, a certain amino acid contained in a sequence of the protein molecule can be substituted by another amino acid in, for example, a protein structure such as a cationic region or a substrate molecule-binding site, without resulting in evident reduction or loss in the interaction binding ability of the protein. The biological functions of a certain protein are determined by the interaction ability and properties thereof. Accordingly, substitution of a specific amino acid can be made in an amino acid sequence or at the level of its DNA coding sequence, and a protein generated by such substitution can still maintain its original properties. Accordingly, various modifications can be carried out in the peptide disclosed in this specification or the corresponding DNA encoding the peptide, without resulting in evident loss in biological utility.

In designing the variants described above, the amino acid hydrophobicity index can be taken into consideration. The importance of the hydrophobic amino acid index in facilitating interactive biological functions in proteins is recognized generally in the art (Kyte, J and Doolittle, R. F. J. Mol. Biol. 157(1):105-132, 1982). The hydrophobicity of amino acids contributes to a secondary structure of a generated protein and defines the interaction between the protein with other molecules (for example, an enzyme, substrate, receptor, DNA, antibody, antigen and the like). Each amino acid is assigned a hydrophobicity index based on its hydrophobicity and charge properties, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is a well known concept in the art that a certain amino acid can be substituted by another amino acid having a similar hydrophobicity index to generate a protein still having similar biological functions (for example, a protein equivalent in enzyme activity). In such an amino acid substitution, the hydrophobicity index is preferably within ±2, more preferably within ±1, still more preferably within ±0.5. It is appreciated in the art that amino acid substitution based on hydrophobicity is effective.

In designing variants, hydrophilicity index can also be considered in the art. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is appreciated that an amino acid can be substituted by another amino acid which has a similar hydrophilicity index and which may provide a biological equivalent. In such amino acid substitution, the hydrophilicity index is preferably within ±2, more preferably within ±1, still more preferably within ±0.5.

As used herein, "conservative substitution" refers to amino acid substitution in which an original amino acid and a substituting amino acid are similar to each other with respect to the hydrophilicity index and/or hydrophobicity index, as described above. For example, amino acids substituted by each other in conservative substitution include, but are not limited to, those with hydrophilicity index or hydrophobicity index within ±2, preferably within ±1, more preferably within ±0.5. Accordingly, examples of the conservative substitution are well-known to those skilled in the art and include, but are not limited to, substitutions between the following amino acids of each group: arginine and lysine; glutamic acid and aspartic acid; serine and threonine; glutamine and asparagine; and valine, leucine, and isoleucine.

As used herein, a "variant" refers to a substance derived from the original polypeptide or polynucleotide by partial modification. Such variants include substituted variants, added variants, deleted variants, truncated variants, allelic variants, and the like. Such variants include, but are not limited to, those having one or several substitutions, additions and/or deletions, or one or more substitutions, additions and/or deletions in their nucleic acid molecule or polypeptide standard. Alleles refer to genetic variants that belong to the same gene locus and that are discriminated from each other. Accordingly, the term "allelic mutants" refers to those variants in the relationship of alleles to a certain gene. Such an allelic mutant usually has a sequence identical or extremely similar to its corresponding allele and usually has almost the same biological activity, but may have a different biological activity in rare cases. The term "species homolog" or "homolog" refers to a sequence which in a certain species, has homology (preferably 60% or more, more preferably 80% or more, 85% or more, 90% or more, or 95% or more homology) with a certain gene at the amino acid or nucleotide level. The method for obtaining such a species homolog is clear from the description of the present specification. An "ortholog" is also referred to as an orthologous gene, which refers to two genes derived from a common ancestor by species differentiation. For example, in a hemoglobin gene family having a multigene structure, human and mouse α-hemoglobin genes are in the relationship of orthologs, while human α-hemoglobin gene and human β-hemoglobin gene are in the relationship of paralog (genes occurring upon gene duplication). Orthologs are useful for estimation of a molecular genealogical tree. Because the ortholog in another species can usually have similar functions as in the original species, the ortholog of the present invention can also be useful in the present invention.

As used herein, the term "conservative variant" or "conservatively modified variant" can be applied to both amino acid sequences and nucleic acid sequences. A conservative variant of a specific nucleic acid sequence refers to a nucleic acid encoding the same or substantially the same amino acid sequence, or to substantially the same sequence as the specific nucleic acid when the nucleic acid does not encode an amino acid sequence. Due to the degeneracy of genetic code, a large number of functionally identical nucleotide sequences encode any predetermined protein sequences. For example, all of the codons GCA, GCC, GCG and GCU encode the amino acid alanine. Thus, in every position where alanine is specified by its codon, the codon can be changed into arbitrary one of the corresponding codons shown above, without changing the encoded polypeptide. Such change in nucleic acid is "silent variant (mutation)", that is, one conservatively modified mutation. Every polypeptide-coding nucleotide sequence herein contains every possible silent mutation of the nucleic acid. It is understood in the art that each codon (excluding AUG which is usually the sole codon encoding methionine and TGG which is usually the sole codon encoding tryptophan) in a nucleic acid can be modified to produce functionally identical molecules. Accordingly, each silent mutation in a nucleic acid encoding a polypeptide is implicitly contained in each described sequence. Preferably, such modification can be achieved so as to avoid substitution of cysteine which is an amino acid having significant effects on the higher-order structure of a polypeptide. The method for modifying such nucleotide sequences includes treatments such as cleavage with restriction enzymes, ligation by treatment with DNA polymerase, Klenow fragment, and DNA ligase, and the like, as well as site-specific nucleotide substitution with a synthetic oligonucleotide and the like (site-directed mutagenesis; Mark Zoller and Michael Smith, Methods in Enzymology, 100, 468-500 (1983)). Methods usually used in the field of molecular biology can also be used in modification.

In the present specification, not only the substitution of amino acids but also the addition, deletion or modification of amino acids can be carried out for preparing functionally equivalent polypeptides. The substitution of amino acids means that the original peptide is substituted with one or more amino acids, for example, 1 to 10 amino acids, preferably 1 to 5 amino acids and more preferably 1 to 3 amino acids. The addition of amino acids means that one or more amino acids, for example, 1 to 10 amino acids, preferably 1 to 5 amino acids and more preferably 1 to 3 amino acids are added to the original peptide strand. The deletion of amino acids means that one or more amino acids, for example, 1 to 10 amino acids, preferably 1 to 5 amino acids and more preferably 1 to 3 amino acids are deleted from the original peptide. The modification of amino acids includes, but is not limited to, amidation, carboxylation, sulfation, halogenation, truncation, lipidation, phosphorylation, alkylation, glycosylation, hydroxylation, and acylation (for example, acetylation). The amino acids to be substituted or added may be naturally occurring amino acids or may be non-natural amino acids or amino acid analogs. Naturally occurring amino acids are preferable.

(Method for Preparing Mutant Polypeptide)

The amino acid deletion, substitution or addition (including fusion) of the polypeptide of the present invention can be carried out by site-directed mutagenesis well-known in the art. Such substitution, addition or deletion of one or more amino acids can be carried out according to methods described in Molecular Cloning, A Laboratory Manual, Second Edition, Cold Spring Harbor Laboratory Press (1989), Current Protocols in Molecular Biology, Supplement 1-38, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), Proc. Natl. Acad. Sci., USA, 81, 5662 (1984), Science, 224, 1431 (1984), PCT WO 85/00817 (1985), Nature, 316, 601 (1985) and the like.

(Method for Measuring Tyrosinase Activity)

Well-known methods for measuring activity can be used for the method for measuring tyrosinase activity. The example includes, but is not limited to, a colorimetric method with t-b-catechol as a substrate.

II. Color Reaction Conditions of the Present Invention

The color reaction method of the present invention representatively comprises the following steps:
(a) mixing peptide and tyrosinase;
(b) incubating the mixture; and
(d) cryopreserving the incubated mixture,
and as needs arise, the color reaction method may:
mix an amino acid at the step (a); and
the method may perform a step of adjusting pH of the mixture, as a step (c), after the step (b) and before the step (d).

The peptide used in the present invention may be natural peptide or modified peptide. While the length of the peptide is not specifically limited, it spans from dimer to pentamer, and preferably trimer to tetramer. The peptide used in the present invention preferably includes at least one tyrosine. While the method for modifying peptide is not particularly limited, it includes amidation, carboxylation, sulfation, halogenation, truncation, lipidation, phosphorylation, alkylation, glycosylation, hydroxylation, and acylation (for example, acetylation). The representative modification is the acylation of an amino group of an amino terminus. When a modified peptide is used, it is preferable to mix an amino acid at the step (a).

The amino acid added instead of peptide is not particularly limited. Preferably, glycine, arginine, valine and histidine can be used. Color tones can be changed by the amino acid added. For example, glycine can give a blue color, arginine can give a blue color, valine can give a green color, and histidine can give a yellow green color.

For the temperature of incubation used in the coloration method of the present invention, any temperature at which tyrosinase works can be used. Typically, the temperature of incubation is 25° C., but the temperature is not limited to this.

The temperature for the cryopreserving used in the coloration method of the present invention ranges, but is not limited to, −80° C. to 0° C., preferably, −50° C. to −10° C., more preferably −40° C. to −20° C., and still more preferably −30° C.

In adjusting pH at the step (c), the pH preferably ranges, but is not limited to, pH 8 to pH 11, more preferably pH 8.5 to pH 10.5, and still more preferably pH 9 to pH 10.

Hereinafter, the present invention will be described in more detail by means of examples or the like; however, the present invention is not limited to those examples or the like.

EXAMPLES

Example 1

Figure 1:
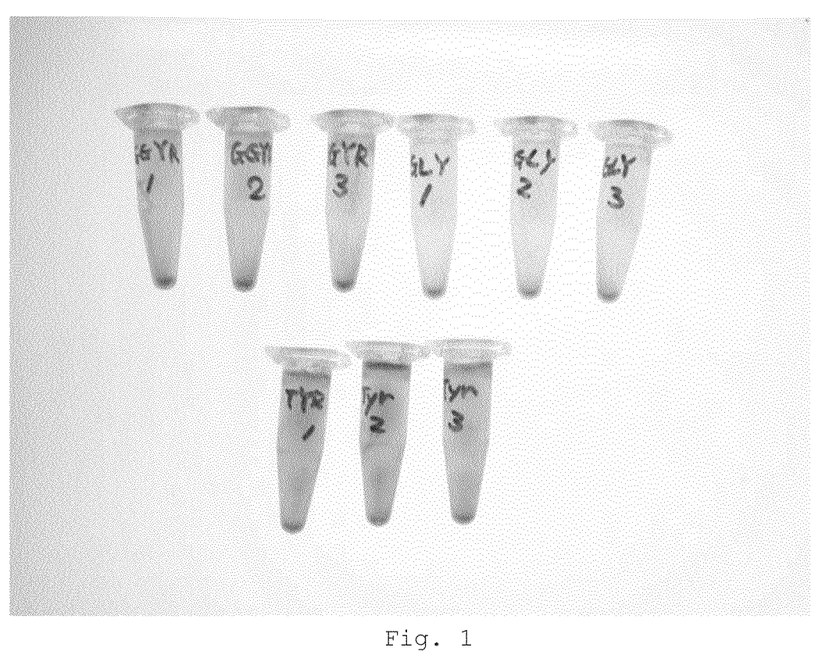
FIG. 1 is a photograph showing results of color reactions using tyrosinase and a GGYR peptide (Tube Nos. 1 to 3), a GLY peptide (Tube Nos. 4 to 6) and tyrosine (Tune Nos. 7 to 9).

Color Reaction by Tyrosinase Enzyme with Peptide and Amino Acid Used as a Substrate A tetramer peptide (SEQ ID NO: 5: Gly-Gly-Tyr-Arg), a trimer peptide (SEQ ID NO: 5: Gly-Leu-Tyr) and an amino acid (tyrosine) were used as a substrate. 2 mM of a substrate and 0.1 U of tyrosinase were added to 16 mL of 25 mM Tris-HCl (pH 7.2) and they were mixed together. The mixed liquid was incubated for 40 minutes at 25° C. and the uptake of $O_2$ was monitored. Subsequently, the mixed liquid was placed on ice for several hours, and it was cryopreserved at −30° C. for 16 hours. As a result, as shown in FIG. 1, a bright green color was produced when a tetramer peptide was used and a bright blue color was produced when a trimer peptide was used, while a brown color was produced when tyrosine was used.

This result proves that color reactions of bright color tones occurred when peptide, and not tyrosine, was used as a substrate of tyrosinase.

Example 2

Use of Modified Peptide

The production of a coloration substance of a green or blue color in Example 1 was presumed as having been made by a reaction that occurred non-enzymatically under a low temperature after quinone production by tyrosinase reaction. Thus, conditions with a possibility of influencing a non-enzymatic reaction after tyrosinase reaction were examined.

A coloration substance production reaction was predicted to occur when quinone was produced by tyrosinase and subsequently allowed to react with an amino group at the N terminus of the substrate non-enzymatically. In light of such prediction, an experiment was conducted using a modified peptide (AcTyr-Val-Gly) blocked by the acetylation of the amino group of the N terminus of the trimer of Tyr-Val-Gly. However, contrary to such prediction, no coloration was observed.

Subsequently, the peptide (substrate) in which an amino group was blocked, was mixed with glycine (Gly) and tyrosinase. The mixture was incubated and cryopreserved at -30° C. A blue color was produced. The production of the blue color is thought to be due to the progress of the coloration substance production reaction by the amino group of the Gly added together with the substrate.

Example 3

Controlling of Color Tones by Adjusting pH after Tyrosinase Reaction

It was thought that optimum pH would be different between the non-enzymatically occurring reaction and tyrosinase reaction. Thus, pH was varied after the tyrosinase reaction and the results were confirmed. Specifically, the experiment was conducted in the following manner.

Figure 2:
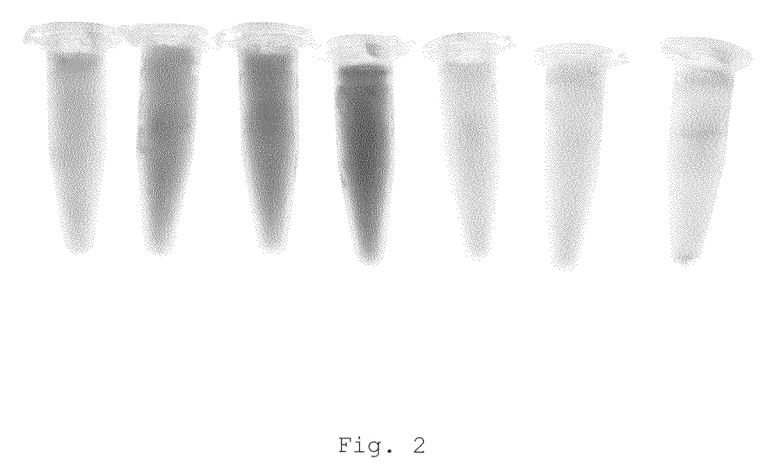
FIG. 2 is a photograph showing coloration resulted from incubating a mixture of an YVG peptide in which an amino group at an N-terminal is acetylated, glycine, and tyrosinase, adjusting the pH and preserving the mixture at low temperature.

2 mM of a substrate (AcTyr-Val-Gly used in Example 2) and 2 mM Gly were mixed with tyrosinase (0.8 U/ml), and the mixture was incubated for 40 minutes at 25° C. (in 16 mL of a 10 mM phosphate buffer solution (pH 8.0)). After enzyme reaction, an appropriate amount of NaOH was added to adjust pH. Next, the reaction mixture was cryopreserved for 16 hours at -30° C. preservation, and the color tone was confirmed. The result is shown in FIG. 2 (Tube No. 1: pH was adjusted to 8.0; Tube No. 2: pH was adjusted to 9.0; Tube No. 3: pH was adjusted to 9.5; Tube No. 4: pH was adjusted to 10; Tube No. 5: pH was adjusted to 10.5; Tube No. 6: pH was adjusted to 11; Tube No. 7: pH was adjusted to 12). This result proves that a change in pH after the tyrosinase enzyme reaction allowed color tones to be changed. That is, this result proves that a change in pH in a non-enzymatic color reaction that occurs after a tyrosinase reaction allows a color tone of a coloration to be changed. In particular, colorations ranging from bright blue to green colors were confirmed as a result of adjusting the pH in the range of 8.0 to 10. On the other hand, when the pH is 10.5 or higher, color reactions resulted in yellow to brown colors.

Example 4

Figure 3:
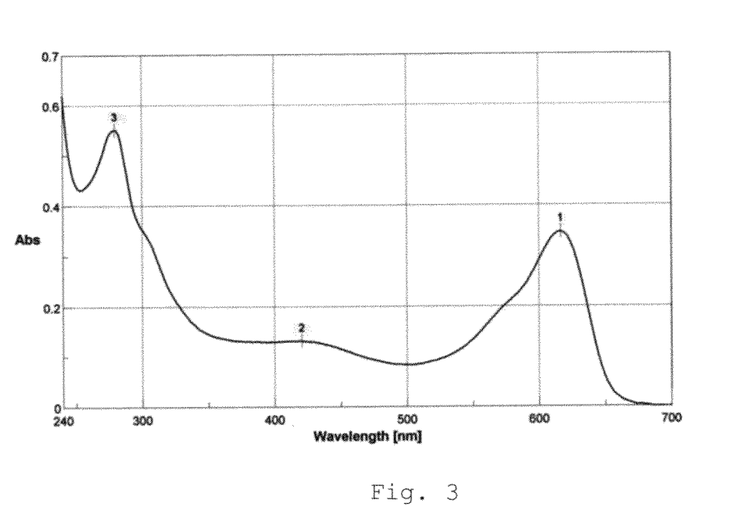
FIG. 3 is a graph showing absorbing spectra of a sample obtained by incubating a mixture of an YVG peptide in which an amino group at an N-terminal is acetylated, glycine, and tyrosinase, preserving the mixture at low temperature, and then preserving it at room temperature.

Evaluation of Color Tones 2 mM of a substrate (AcTyr-Val-Gly used in Example 2) and 2 mM Gly were mixed with tyrosinase (0.8 U/ml), and the mixture was incubated for 40 minutes at 25° C. (in 16 mL of a 10 mM phosphate buffer solution (pH 8.0)). The mixed liquid was placed on ice for several hours, and it was cryopreserved at -30° C. preservation for 16 hours. The mixed liquid was then thawed at room temperature and was left out at room temperature for three days. Absorption spectra were measured using a quartz cuvette having a 0.1 mm optical path length. The result is shown in FIG. 3. The peak of "1" was 616.5 nm. The peak of "2" was 420 nm. The peak of "3" was 279.5 nm. Based on these results, the following consideration was given. The absorbance of a 0.1 cm cell at 616.5 nm was 0.34626. Suppose all the 2 mM substrate reacted, the molar absorbance coefficient would be $1,730 M^{-1} cm^{-1}$. Thus, from the above-mentioned result, it was confirmed that a blue color was strong. While the actual reaction was conducted at 25° C., the dissolved oxygen level at 25° is 253 μM, and this is presumed to be the upper limit of the reaction. Theoretically, if the maximum amount of available substrate is 253 μM, and not 2 mM, the calculated absorbance coefficient would be $13,686 M^{-1} cm^{-1}$ and the blue color would be even stronger.

INDUSTRIAL APPLICABILITY

According to the present invention, a color reaction for coloration of bright green to blue colors can be easily provided by using peptide and tyrosinase.

[Sequence Listing Free Text]

SEQ ID NO: 1: a nucleic acid sequence of a gene encoding a tyrosinase tyr1 derived from *Pholiota nameko* (*Pholiota microspora*)

SEQ ID NO: 2: an amino acid sequence of a tyrosinase tyr1 derived from *Pholiota nameko* (*Pholiota microspora*)

SEQ ID NO: 3: a nucleic acid sequence of a gene encoding a tyrosinase tyr2 derived from *Pholiota nameko* (*Pholiota microspora*)

SEQ ID NO: 4: an amino acid sequence of a tyrosinase tyr2 derived from *Pholiota nameko* (*Pholiota microspora*)

SEQ ID NO: 5: an amino acid sequence of a tetramer peptide used in the Examples

The invention claimed is:

1. A coloration method comprising the steps of:
   (a) mixing peptide and tyrosinase;
   (b) incubating the mixture;
   (c) adjusting the pH of the mixture from 8 to 11;
   (d) a color reaction for coloration of bright green to blue colors with the mixing of tyrosinase and peptide; and
   (e) cryopreserving the incubated mixture
   wherein the tyrosinase is obtained from *Pholiota nameko* and is encoded by a polynucleotide selected from the group consisting of:
   (1) a polynucleotide consisting of a base sequence set forth in SEQ ID NO: 1 or 3;
   (2) a polynucleotide encoding the amino acid sequence set forth in SEQ ID NO: 2 or 4;
   (3) a polynucleotide hybridizing to a fully complementary strand of any one of the polynucleotides (1) to (2) under highly stringent conditions;
   wherein the highly stringent condition related to hybridization and washing is 0.0015M sodium chloride, 0.0015M sodium citrate, 65-68° C., 50% formamide, and 42° C.,
   and wherein the amino acid at the N-terminus of the peptide is glycine.

2. The coloration method according to claim 1, wherein the length of the peptide ranges from dimer to pentamer.

3. The coloration method according to claim 1, wherein the length of the peptide ranges from trimer to tetramer.

4. The coloration method according to claim 1, wherein the cryopreserving is performed at a temperature ranging from −80° C. to 0° C.

5. The coloration method according to claim 1, wherein the cryopreserving is performed at a temperature ranging from −40° C. to −20° C.

6. The coloration method according to claim 1, wherein the cryopreserving is performed at a temperature of −30° C.

7. The coloration method according to claim 1, wherein at step (a), amino acid is further mixed.

8. The coloration method according to claim 1, wherein at step (a), glycine is further mixed.

9. The coloration method according to claim 1, wherein: the peptide is a peptide in which an N terminus is modified; and glycine is further mixed at step (a).

10. The coloration method according to claim 9, wherein modification of the N terminus is acetylation of an amino group of the N terminus.

11. The coloration method according to claim 1, wherein the peptide consists of an amino acid sequence as set forth in SEQ ID NO: 5.

* * * * *